United States Patent [19]

Bradcovich et al.

[11] Patent Number: 5,490,297

[45] Date of Patent: Feb. 13, 1996

[54] MOBILE IMAGING TABLE

[75] Inventors: James M. Bradcovich, Akron; Richard J. Frankovich, North Olmsted, both of Ohio

[73] Assignee: Beta Medical Products, Inc., Akron, Ohio

[21] Appl. No.: 299,911

[22] Filed: Sep. 1, 1994

[51] Int. Cl.[6] .............................. A61G 7/012; A61G 7/05
[52] U.S. Cl. .................... 5/601; 5/611; 108/144
[58] Field of Search ............................... 5/601, 611, 600, 5/81.1, 86.1; 108/143, 144; 378/209

[56] References Cited

U.S. PATENT DOCUMENTS

| | | | |
|---|---|---|---|
| 3,980,288 | 9/1976 | Mitchell et al. | 5/601 |
| 4,568,071 | 2/1986 | Rice | 5/601 |
| 4,842,259 | 6/1989 | Rice | 5/601 |
| 4,912,787 | 4/1990 | Bradovich | 5/601 |
| 4,944,501 | 7/1990 | Sireul et al. | 5/601 |
| 4,991,242 | 2/1991 | Brown | 5/601 |
| 4,995,067 | 2/1991 | Royster et al. | 5/601 |
| 5,077,780 | 12/1991 | Lee, Jr. | 5/601 |
| 5,197,474 | 3/1993 | Englund et al. | 5/601 |
| 5,199,123 | 4/1993 | Sireul et al. | 5/601 |
| 5,201,088 | 4/1993 | Larsson | 5/610 |
| 5,237,600 | 8/1993 | Kamata | 5/611 |
| 5,272,776 | 12/1993 | Kitamura | 5/81.1 |
| 5,285,733 | 2/1994 | Waibel | 108/144 |
| 5,305,749 | 4/1994 | Li et al. | 5/601 |
| 5,394,809 | 3/1995 | Feldpausch et al. | 108/144 |
| 5,427,035 | 6/1995 | Grahl | 108/144 |

OTHER PUBLICATIONS

Thomas Register, vol. 1, pp. 1771 to 1781, published by Thomas Publishing Co., New York, NY 1992.

THK LM System Linear Motion Systems, published by THK Co., Ltd., Tokyo, Japan, 1993, pp. 48, 49, 58 and 59.

*Primary Examiner*—Alexander Grosz
*Attorney, Agent, or Firm*—Oldham & Oldham Co.

[57] ABSTRACT

Mobile imaging table for transporting a patient and for imaging the patient using a radiographic imaging apparatus such as a CT scan, MRI apparatus, or X-ray. The mobile imaging table comprises a generally rectangular lower frame member supported on rollers, a vertically movable upper frame member, a longitudinally and horizontally movable table top which is movable between a first position for transport of a patient and a second position for imaging, and at least one linear bearing assembly for guiding the vertical movement of the upper frame member. Each linear bearing assembly comprises at least two telescoping vertical plates (or other linear bearing support members) and each vertical plate has at least one (preferably two) vertically extending linear bearings mounted thereon. Either a pair of longitudinally extending linear bearing assemblies (one on either side of the mobile imaging table) or a single transverse linear bearing assembly may be provided. Deflection of the table top in the second position is very slight, making possible precise placement of a patient for imaging so that a focused radiographic image may be obtained.

6 Claims, 5 Drawing Sheets

MOBILE IMAGING TABLE

TECHNICAL FIELD

This invention relates to a device for transporting a patient and for supporting the patient for a diagnostic imaging procedure, such as CT scan, MRI, or X-ray. More particularly, this invention relates to a mobile imaging table which enables hospital or medical center personnel to transport a patient from the patient's room to a radiographic imaging apparatus such CT scan, MRI, or X-ray and to support the patient for imaging by such apparatus, without the necessity of transferring the patient from one patient support device to another.

DESCRIPTION OF THE PRIOR ART

Radiographic imaging devices, including CT scanners, MRI devices, and x-ray devices are widely used in medical centers such as hospitals for diagnostic purposes. For imaging, it is necessary to support a patient on a bed or table which includes a patient-supporting structure (e.g., a table top) which is radiation permeable and at the same time strong enough to support the patient. Typically, the table has a fixed base which is adjacent to the imaging apparatus. The table top may be linearly movable, e.g., between a first position directly over the base and outside the range of radiation of the imaging device, and a second position in which the table top extends outwardly beyond the base and is within the range of radiation of the imaging device.

A patient who is to undergo diagnostic imaging is typically brought from another part of the hospital, for example a patient's room, to the site of the imaging apparatus on a gurney or other transport device. The patient is then transferred from the gurney to the imaging table while the table top is in its first position outside the imaging apparatus. The table top is then moved until a desired portion of both table top and the patient's body are within radiation range. After imaging is complete, the table top is returned to its first position, and the patient is then transferred back to a gurney for transport to another location in the hospital.

The arrangement just described involves inconvenience and possible injury to the patient as the patient is being transferred from a gurney to the imaging table and back again after imaging is complete.

Devices which are useful both for transporting a patient from one location to another (from a patient's room to the imaging apparatus) within the hospital and also for supporting the patient during imaging, are also known. One problem with such devices is that they are not capable of positioning a patient for imaging as precisely as are the imaging tables which are supported on a fixed base adjacent to the imaging apparatus. Therefore, devices which combine the functions of patient transport and patient support for imaging have not gained wide-spread use.

There exists a need for a mobile imaging table which can serve both to transport a patient within a medical center to the site of an imaging apparatus and to support a patient for imaging, wherein the patient may be positioned for imaging with a high degree of precision.

SUMMARY OF THE INVENTION

This invention provides a mobile imaging table comprising:

(a) a lower frame member supported on rollers;

(b) a vertically movable upper frame member;

(c) a radiation permeable table top for supporting a patient, said table top being movable relative to said upper frame member between a first position and a second position;

(d) vertical linear bearings for guiding vertical movement of said upper frame member; and (e) drive means for raising and lowering said upper frame member.

Linear bearings are mounted on telescoping vertical plates or other telescoping rigid support members. The linear bearings and the plates form one or more linear bearing assemblies, wherein each linear bearing assembly comprises at least two plates in telescoping relationship and each plate has at least one linear bearing mounted thereon.

BRIEF DESCRIPTION OF THE DRAWINGS

In the drawings:

FIG. 1 is a side elevational view of a mobile imaging table according to a first and preferred embodiment of the invention FIG. 2 is an enlarged side elevational view of a portion of the mobile imaging table shown in FIG. 1.

FIG. 3 is a side elevational view of a linear bearing assembly or set according to this invention, shown in a lowered position.

FIG. 4 is aside elevational view of a telescoping linear bearing assembly or set according to this invention, shown in a raised position.

FIG. 5 is a top plan view of a portion of the device shown in FIG. 1.

BEST MODE FOR CARRYING OUT THE INVENTION

Figure 1:
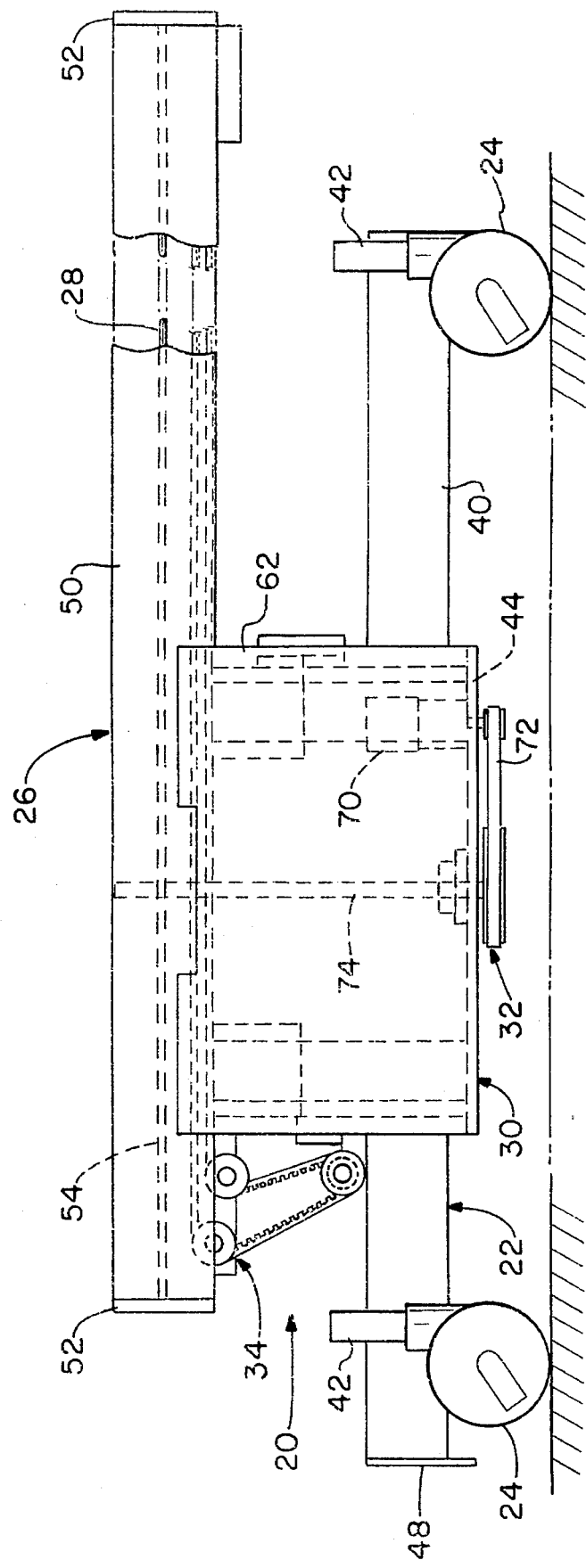
FIGS. 1–5 illustrate a mobile imaging table according to a first embodiment of the invention.
Figure 2:
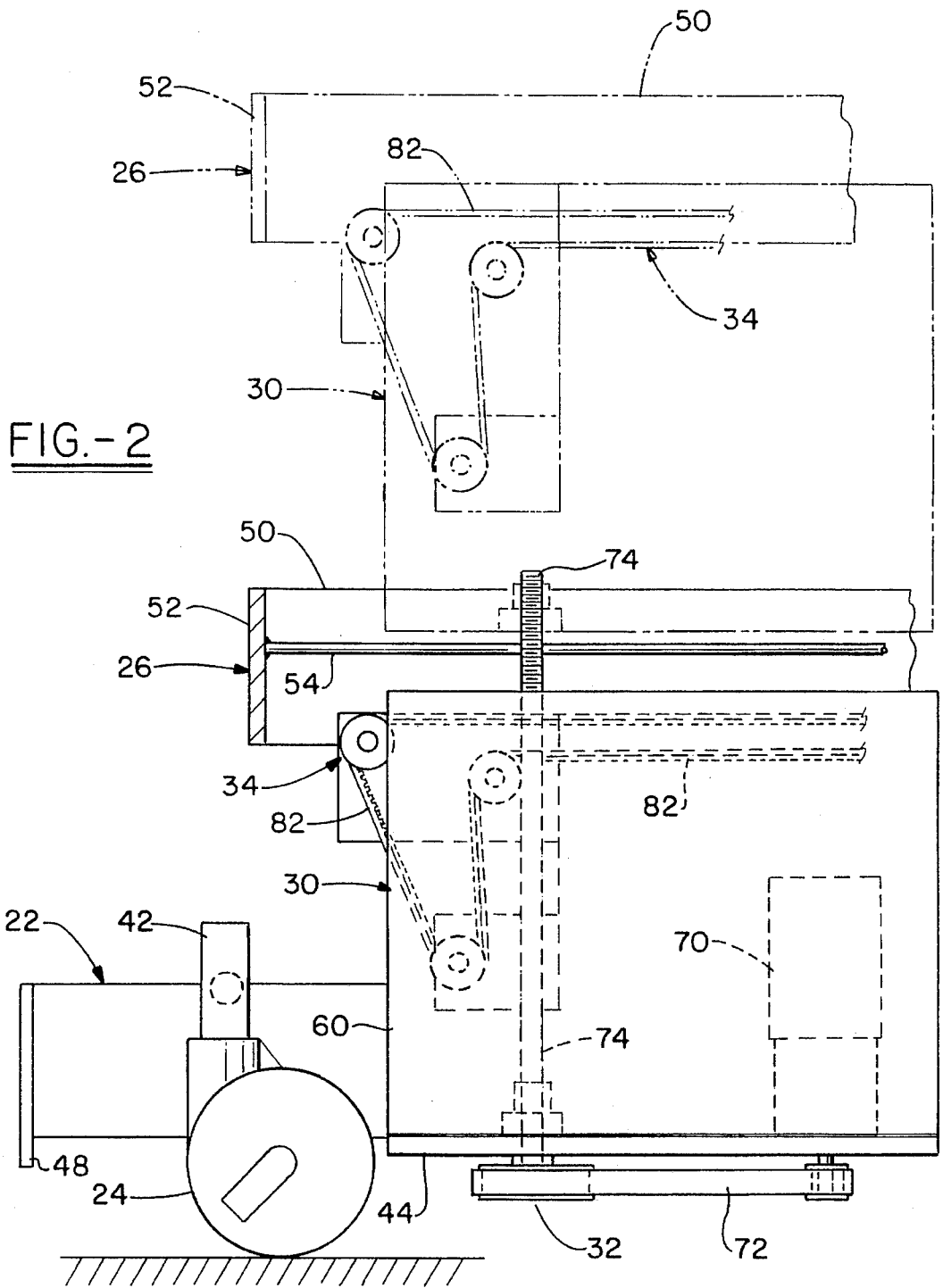

This invention will now be described in detail with reference to specific embodiments thereof, including the best mode and preferred embodiment.

FIGS. 1–5 illustrate the first and preferred embodiment of this invention.

Referring now to FIGS. 1–5, 20 is a mobile imaging table according to this invention. The mobile imaging table 20 of this invention comprises an open generally rectangular lower frame member 22 supported on rollers 24; a vertically movable open generally rectangular upper frame member 26 which is vertically movable relative to the lower frame member; and a radiation permeable table top 28 for supporting a patient both for transport and for imaging. The table top 28 is horizontally movable between a first or retracted position for transport and a second or extended position for imaging, as will be described hereinafter in detail.

The mobile imaging table 20 of this invention further comprises a pair of vertical linear bearing assemblies 30 on opposite sides of the mobile imaging table 20 for guiding vertical movement of the upper frame member 26; first drive means 32 for raising and lowering the upper frame member 26; and second drive means 34 for causing horizontal movement of the table top 28 between the first and second positions as described above.

The lower frame member 22 composes a first pair of parallel beams 40 which extend longitudinally and form the two longer sides of the rectangular lower frame member; and a second pair of beams 42 which extends transversely and form the two shorter sides (or ends) of the rectangular lower frame member 22. Each of the two shorter sides 42 intersects each of the two longer sides 40 at right angles, forming a rectangle which has four corners and a perimeter defined by sides 40 and 42. The lateral beams 42 may extend beyond the longitudinal beams 40 as shown. A horizontal base plate 44 may extend from one longitudinal beam 40 to the other longitudinal beam 40 at a midsection of the device 20 (i.e., on either side of the longitudinal center of the device), providing additional reinforcement for the frame and providing a mounting base for a motor as will be hereinafter described. Additional reinforcing members, as for example a second horizontal plate extending from one longitudinal beam 40 to the other at a rearward portion of the lower frame member, may be provided as desired. A vertical front bumper plate 48 is mounted on the front end of the lower frame member 22 in front of the front transverse beam 42.

Upper frame member 26 is a vertically movable generally rectangular frame formed by a pair of longitudinally extending beams 50 and a pair of transversely extending beams 52. The longitudinal beams 50 may be vertical plates. The transversely extending beams 52 are channel shaped (or U-shaped) so that the main or horizontally extending portion of each of these beams is at a lower elevation than that of the upper edge of longitudinal beams 50. This construction is important for the front transverse beam 52 in order to permit horizontal reciprocable or sliding movement of the table top 28 in the longitudinal direction (this construction is optional for the rear transverse beam 52). A pair of longitudinally extending guide rails 54, which are preferably Thompson rails, are affixed to and spaced slightly from inside surfaces of the longitudinal beams 50. A reciprocating carriage 56 rides on guide rails 54 and supports table top 28. Thus the guide rails 54 guide the horizontal reciprocating movement of table top 28. The two longitudinal beams 50 and the two transverse frames 52 together form an open rectangle and define tie perimeter of that open rectangle.

Rollers 24 are secured to the lower frame member 22, e.g., at the ends of transverse beams 42, in a rectangular arrangement. These rollers, which may be conventional casters of the type used for mobile gurneys, carts, etc., extend downwardly from the lower frame member.

Figures 3, 4:
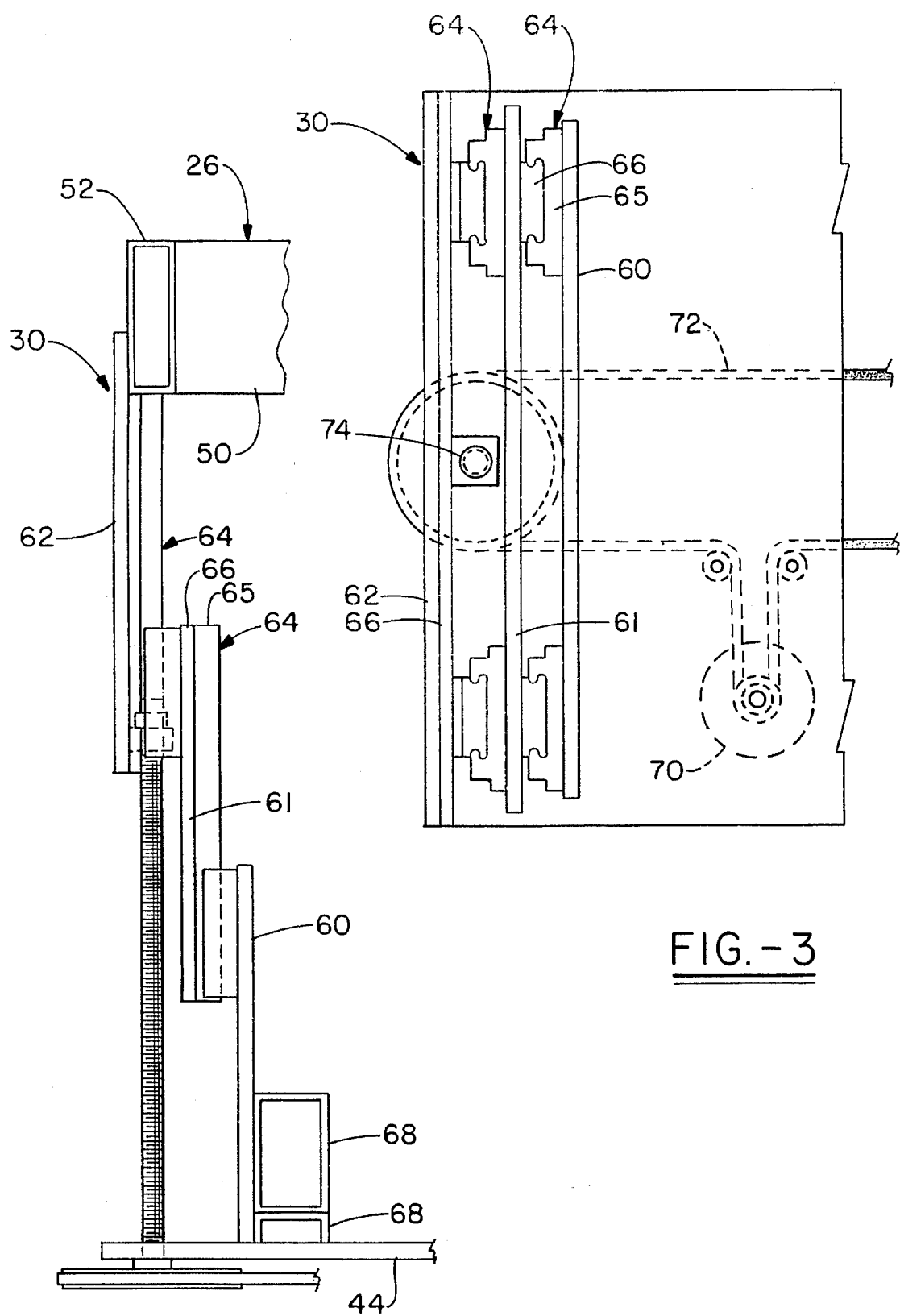
Figure 5:
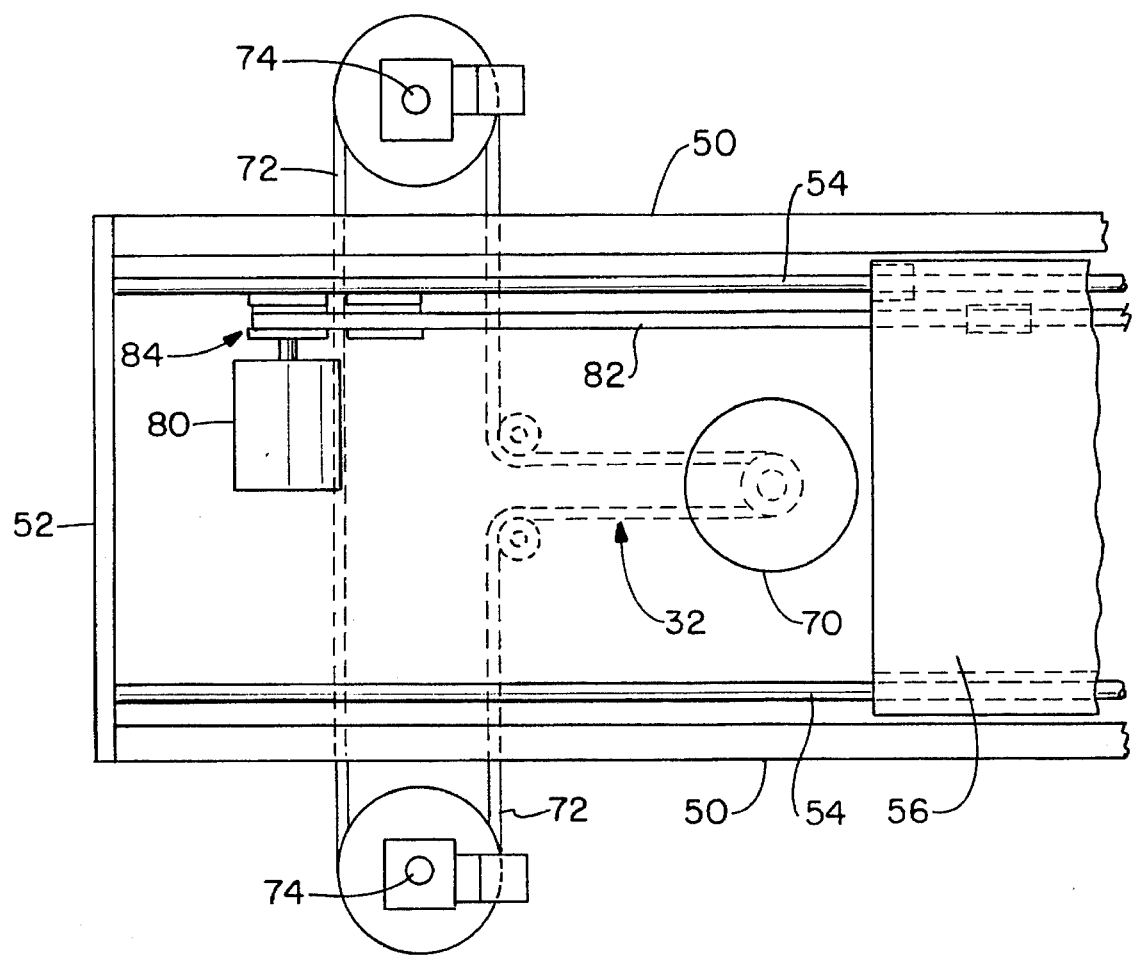

A pair of vertically extending plural stage linear bearing assemblies 30, shown in FIGS. 3 and 4, guide the upward and downward movement of upper frame member 26. FIG. 3 shows a linear bearing assembly in a first or lowered position. FIG. 4 shows the linear bearing assembly in a second or raised position. These linear bearing assemblies are provided on the two longer sides of the device 20. Each linear bearing assembly or set comprises a set (i.e., a plurality) of vertical longitudinally extending plates 60, 61, and 62 (usually two or three plates as shown are provided) arranged in telescoping fashion. Each plate is rectangular, having horizontal (upper and lower) and vertical (forward and rearward) edges. Mounted on each plate are a pair of longitudinally spaced linear bearings 64 which are mounted near the vertical edges of each plate. Each linear bearing comprises a vertical guideway 65, which is affixed to a plate 60 or 61, and a vertically extending and vertically movable slide 66, which is affixed to a plate 61 or 62 and slides in a guide channel formed by the guideway 65. The guideway 65 is affixed to the lower of a pair of adjacent plates (e.g. to plates 60 and 61) and the slide is affixed to the higher plate (e.g., 61 and 62) of the pair. Linear bearings per se are well known in the art and the structure of the linear bearings used herein may be conventional.

Each linear bearing assembly or set 30 comprises a lowermost plate 60 which is affixed (e.g., by welding or riveting through one or more base members or channels 68) to the lower frame member 22 and preferably to a longitudinally extending beam 40 thereof, and an uppermost plate 62 which is affixed to the upper frame member 26 (e.g., to a longitudinally extending beam 50 thereof). The assembly 30 may include one or more intermediate plates 61. Each of the plates includes means for engaging the next adjacent plate, whether higher or lower, lift any intermediate plates by gravity as the upper frame member 26 and the uppermost plate are lifted, and conversely to lower any intermediate plates as the upper frame member 26 and uppermost plate are lowered.

The center of gravity of the device 20 should fall between the forward and rearward vertical edges of the plates 60, 61, and 62 forming a plate assembly, whether the table top 28 is in its normal (i.e., retracted) or its extended position, and whether or not a patient is lying on the table top 28. This is highly desirable for stability of the device 20 and in order to minimize deflection of the table top 28 when it is extended. The width and placement of plates 60, 61, and 62 in the longitudinal direction is such as to achieve this.

Other support members may be used in place of the vertical plates 60, 61, 62 for supporting the linear bearing if desired. For example, a pair of vertical linear bearings may be held in fixed relationship by a plurality of spaced horizontal rigid slats. A linear bearing assembly or set would then comprise two or more pairs of linear bearings and the slats on which they are mounted, arranged in telescoping relationship.

The first drive means 32 for raising and lowering the upper frame member 26 comprises a motor 70 mounted on base plate 44, a belt drive 72 driven by motor 70, and a vertical screw 74, which are driven by the motor 70 and belt drive 72. The screw 74 engages an uppermost plate 62 of a linear bearing assembly 30, causing plate 62 and upper frame member 26 to ascend when the screw is turned in one direction, and to descend when the screw is turned in the other direction. (A pair of telescoping screws may be used if desired).

The plates 60, 61, and 62 forming a plate assembly 30 move from a fully retracted first position, shown in FIG. 3, in which the upper frame member 26 is at its lowest level and the individual plates 60, 61, and 62 are essentially aligned one behind the other, to an extended second position, shown in FIG. 4, in which the upper frame member 26 is at its upper level of travel and each of the plates 60, 61, and 62 as seen in side view is substantially fully exposed.

Radiation permeable (or radiotranslucent) table top or pallet 28 is rectangular and of any convenient length and width. The length and width of the radiation permeable table top 28 are less than the length and width, respectively, of the upper frame member 26. The radiation permeable table top 28 may be of any convenient length which is long enough to support most patients, e.g., 77 to 78 inches (196 to 198 cm).

Figure 6:
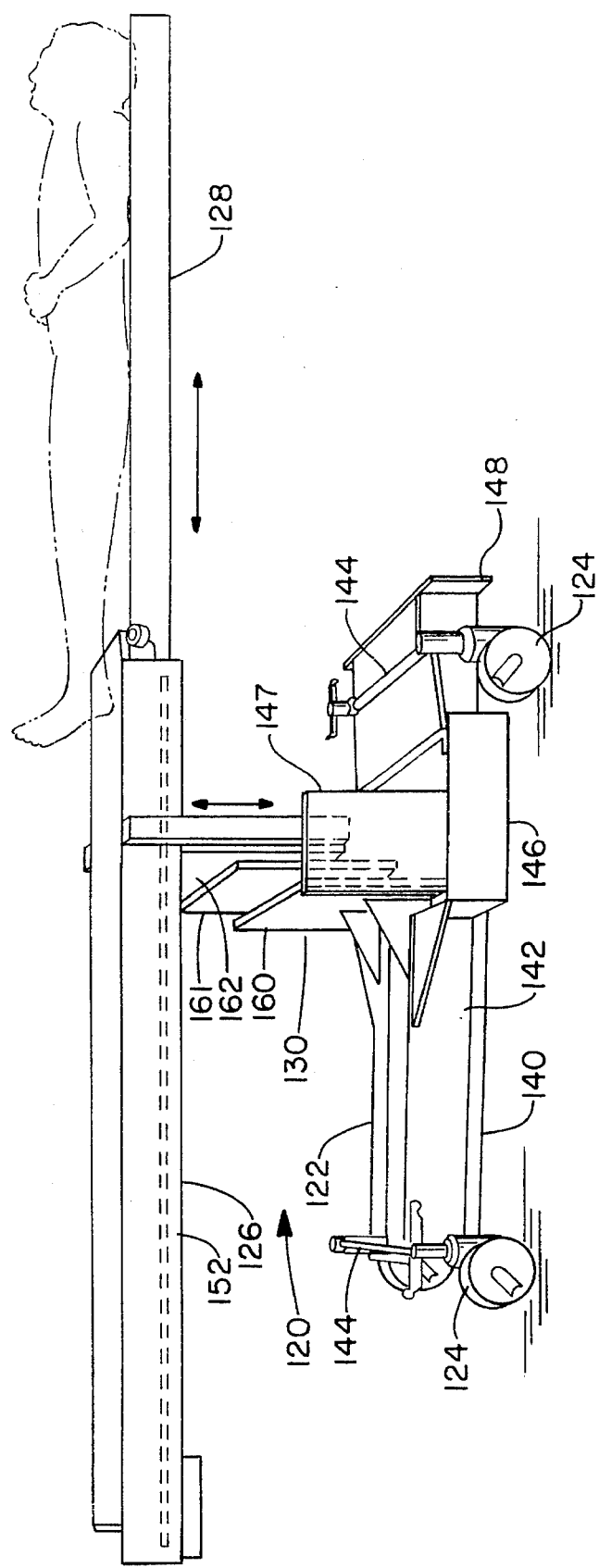
FIG. 6 is a side elevational view of a mobile imaging table according to a second embodiment of the invention.

The radiation permeable table top 28 is horizontally and longitudinally movable between a first or retracted position, as shown in FIG. 1, and a second or extended position, shown in FIG. 6. (While structural details of the respective embodiments shown in FIGS. 1 and 6 differ, as will be discussed in detail hereinafter, movements of the table top in these embodiments are similar.) In the first or retracted position, the entire table top is disposed within the perimeter of the upper frame member 26. This is the position for patient transport and for patient loading and unloading. In the longitudinally extended second position, most of table top 28 extends beyond the outline or perimeter of the upper frame member 26. Table top 28 in its extended position is cantilevered and is supported only in proximity with a rearward end thereof. The second or extended position of the table top 28 is the position for imaging. The table top 28 may have any convenient length of travel, e.g., 60 inches (152 cm) from the first to the second position.

Table top 28 is driven from its first position to its second position and back by means of the second drive means 34. Second drive means 34 comprises a motor 80 which may be affixed to the upper frame member 26 and specifically to the forward transverse beam 52 thereof, and a drive belt 82 which is driven by motor 80. Drive belt 82 engages the table top 28 to drive the table top between its first and second positions.

While both the first drive means 32 and the second drive means 34 are illustrated herein as being motor driven, it shall be understood that either or both drive means may be manually powered (although motor drives are preferred). For example, a conventional screw jack may be used a first drive means 32 to raise and lower the upper frame member 26. The slidable carriage 56 and patient support table top 28 mounted thereon may be moved by hand between the first and second positions, since relatively little power is required for this purpose. If hand movement is relied on, locking means should be provided to lock the table top 28 into its first and into its second positions.

In operation, a patient is transferred from a hospital bed to the table top 28 of device 20 while the upper frame member 26 and consequently also the table top 28 are in their lowermost positions and the table top 28 further is in its first or retracted position. The mobile imaging table 20 with a patient aboard is wheeled through hospital corridors to the site of an imaging apparatus with the upper frame member 26 in its lowermost position and the table top 28 retracted. When the mobile table 20 with a patient aboard reaches an imaging site, (i.e., the site of an imaging apparatus such as a CT scan, an MRI device, etc.) the upper frame member 26 is raised to a suitable height for imaging. This may vary from one imaging apparatus to another and therefore may require lifting of the upper frame member either to the full extent possible or to some intermediate position. Table top 28 rises and is lowered with the upper frame member 26. Raising and lowering are accomplished by means of the first drive means 32 as previously described. Then the table top 28 is moved by means of the second drive means 34 from its first or retracted position to its second or extended position, in which the table top and a patient lying thereon in position for imaging. When imaging has been completed, the process is reversed. Table top 28 is returned to its first or retracted position, and then the upper frame member 26 and table top 28 are lowered to the lowermost position for transport of the patient back to a patient bed.

The imaging table of the present invention can be used for imaging in either a tunnel-type imaging apparatus or in an imaging apparatus having open sides and one open end.

Little deflection of the table top 28 and its extended position takes place in the first embodiment of this invention described so far. This is highly desirable since a precise positioning of the table top 28 and a patient thereon may be necessary to assure an image that is properly focused. Deflection herein is defined as a variation of the actual position of table top 28 from a strictly horizontal position (i.e., a horizontal extension of the table top in its retractable position). In a representative test, table top 28, 78 inches long, is extended to the maximum extent possible, i.e., 60 inches, out the head end from its first or retracted position. A 300 lb. test weight, centered at 39 inches from the head end of the table top 28, causes a deflection of 0.39 inch (0.65 inch of deflection per 100 inches of horizontal extension). This small degree of deflection is comparable to that attainable in a cantilevered retractable imaging table top which forms part of an imaging table mounted on a fixed base.

The mobile imaging table 20 of the present invention offers all of the advantages of both a fixed imaging table and a mobile imaging table. This invention achieves in a mobile imaging table a low degree of deflection of an imaging table top which is heretofore found only in fixed imaging tables. Furthermore, this is achieved according to the present invention in a table top which in its extended position is supported in cantilevered fashion and does not require any support from the imaging apparatus. This, of course, is a very significant advantage, since rollers, guideways, etc., within an imaging apparatus may require components which are radio-opaque (metallic spools or cores for rollers, for example). At the same time, the device under the present invention has the advantage of mobility.

The linear bearing assemblies 30 impart to the vertical movements of upper frame member 26 a high degree of precision with virtually no "wobble". The vertical path of travel of the upper frame member 26 is virtually precisely vertical as a result of using linear bearings assemblies 30 as described herein for guiding the vertical movement of the upper frame member. Other means for lifting and lowering an upper frame member of a patient transport and imaging device are known, but they do not provide the same precise positioning of an upper frame member when raised either partially or to the fullest extent possible, that one achieves with the apparatus of this invention. Very precise and stable positioning of the upper frame member in a raised position makes it possible to achieve a very low degree of deflection in a table top 28 in its extended position.

This invention will now be described in further detail with respect to a second embodiment thereof as shown in FIG. 6 of the drawings. In this second embodiment, the longitudinally extending linear bearings assemblies 30 of the first embodiment are replaced with a transversely extending linear bearing assembly 130. A greater degree of deflection is obtained. In a representative apparatus in according to this second embodiment, a vertical deflection of 0.56 inch was observed at 39 inches extension of the table top 78 inches long with a test weight of 300 pounds centered 39 inches from the forward or unsupported end. This amounted to 1.44 inches of vertical deflection per 100 inches of extension in the longitudinal direction-more than twice the amount than encountered in the first embodiment.

The second embodiment will now be described in detail.

Referring to FIG. 6, 120 is a mobile imaging table as a whole according to a second embodiment of this invention. The mobile imaging table of the second embodiment comprises a lower frame member 122 which is supported on rollers 124 and a vertically movable upper frame member or bed 126 which supports a horizontally and longitudinally movable radiation transparent table top (or pallet) 128. The mobile imaging table (or mobile patient support device) 120 of the present invention may further comprise a transversely extending linear bearing assembly 130, a first drive means (not shown) for raising and lowering the upper frame member 126, and a second drive means (not shown) for causing horizontal movement of the table top 128 between a first or retracted position and a second or extended position shown in FIG. 6. The drive means for raising and lowering the upper frame member 126, and the drive means for causing longitudinal horizontal movement of the table top 128 have not been shown because these may be similar or identical to their counterparts 32 and 34, respectively, of the first embodiment.

The lower frame member comprises a horizontal rectangular metal base plate 140, a pair of upright longitudinally extending metal plates 142 which form longitudinally extending sides, a vertical transversely extending metal beams 144 at front and back ends of the lower frame member. The lower frame member 122 may further comprise a box-like structure 146 having four vertical sides and an open top, for housing a linear bearing assembly to be described later. A pair of upstanding vertical plates 147, extending upwardly from the box-like structure 146, may be provided at the sides of the lower frame member 122 for concealing and protecting the linear bearing assembly. A vertical front bumper plate 148 may be provided at the end of the lower frame member 122.

Rollers or casters 124 are mounted in a conventional manner in a rectangular array slightly outward of the four corners of the lower frame member 122 which is essentially rectangular in shape.

Upper frame member 126 is essentially rectangular in shape, and may be generally similar in structure to the upper frame member 26 of the first embodiment. Consequently, the structure of the upper frame member (or bed) is not described in detail. A pair of longitudinally extending guide rails, not shown and disposed in close proximity with the inside surfaces of side 152, guide the longitudinal horizontal travel of a carriage (not shown) on which the table top 128 is mounted. These guide rails and the carriage may be similar to the Thompson rails 54 and carriage 56, respectively, of the first embodiment.

The radiation permeable (or radiotranslucent) table top or pallet 128 may be identical or similar to its counterpart 28 or the first embodiment. Pallet 128 is rectangular and may be of any desired length. A preferred length is about 77 to 78 inches (196 to 198 cm).

The second embodiment utilizes a single linear bearing assembly or set 130 which extends transversely. The linear bearing assembly or set 130 is similar to each of the linear bearing assemblies 30 of the first embodiment. Linear bearing assembly 130 comprises a plurality of vertical transversely extending rectangular plates 160, 161, and 162 (three such plates are shown).

The lowermost plate 160 is affixed to the lower frame member 122, and the uppermost plate 162 is affixed to the upper frame member 126. The intermediate plate 161 is an idler which travels up and down with uppermost plate 162. The plates 160, 161, and 162 are provided with conventional means, e.g., limit stops, for interengaging an adjacent plate as the upper frame member 126 and with it the uppermost plate 162 are raised and lowered.

A first drive means comprising a drive motor and a drive screw driven thereby may be provided for raising and lowering the upper frame member 126. This first drive means may be similar to its counterpart 32 in the first embodiment.

Second drive means (not shown), which may be similar to the second drive means 34 of the first embodiment, may be provided for driving the radiotranslucent table top 128 horizontally and longitudinally.

The device of the second-embodiment is lighter in weight and less expensive to manufacture than the device of the first embodiment. However, deflection in an extended table top in the second embodiment is much greater, i.e., approximately twice as much, as the deflection in an extended pallet of the first embodiment at a similar amount of extension and under a similar load. Therefore, the mobile imaging table of the first embodiment is ordinarily preferred, except where either weight or economy is important and the amount of deflection in a device of the second embodiment is acceptable.

While this invention has been described with reference to specific embodiments, including the best mode and preferred embodiment, it will be apparent that variations and modifications can be made by those of ordinary skill in the art without departing from the scope or spirit of the present invention.

What is claimed is:

1. A mobile image table comprising:
   (a) a lower frame member supported on rollers;
   (b) a vertically movable upper frame members;
   (c) a radiation permeable table top for supporting a patient, said table top being longitudinally movable between a first position within a perimeter of said upper frame member and a second position in which a major portion of said table top extends beyond said perimeter of said upper frame member;
   (d) a pair of linear bearing assemblies for guiding vertical movement of said upper frame member relative to said lower frame member, each of said linear bearing assemblies comprising a plurality of vertically extending rigid plates in telescoping relationship and comprising at least one pair of adjacent plates, said plates including a lowermost plate affixed to said lower frame member and an uppermost plate affixed to said upper frame member, and at least one vertically extending linear bearing associated with each pair of adjacent plates, each said vertically extending linear bearing comprising at least one slide means slidably connected to a guideway, wherein said slide means is affixed to one plate and said guideway is affixed to an adjacent plate; and
   (e) drive means for raising and lowering said upper frame member.

2. A mobile imaging table according to claim 1, said mobile imaging table comprising a pair longitudinally extending linear bearing assemblies disposed on opposite sides of said mobile imaging table.

3. A mobile imaging table according to claim 1 wherein said linear bearing assembly extends transversely.

4. A mobile imaging table according to claim 1 wherein said upper frame member and said table top are each essentially rectangular and wherein said upper frame member has greater length and greater width than said table top.

5. A mobile imaging table according to claim 1 including second drive means for moving said table top between said first position and said second position.

6. Mobile imaging table according to claim 1 wherein each of said linear bearing assemblies further includes at least one intermediate plate positioned between said lowermost plate and said uppermost plate.

* * * * *